United States Patent [19]

Von Der Saal et al.

[11] Patent Number: 4,835,167
[45] Date of Patent: May 30, 1989

[54] TRICYCLIC BENZOTRIAZOLES, PROCESSES FOR THE PREPARATION THEREOF AND PHARMACEUTICAL COMPOSITIONS CONTAINING THEM

[75] Inventors: Wolfgang Von Der Saal, Weinheim; Walter-Gunar Friebe, Mannheim; Alfred Mertens, Schriesheim; Bernd Müller-Beckmann, Grünstadt; Gisbert Sponer, Laudenbach, all of Fed. Rep. of Germany

[73] Assignee: Boehringer Mannheim GmbH, Mannheim, Fed. Rep. of Germany

[21] Appl. No.: 80,658

[22] Filed: Aug. 3, 1987

[30] Foreign Application Priority Data

Aug. 7, 1986 [DE] Fed. Rep. of Germany ....... 3626664

[51] Int. Cl.$^4$ ............... C07D 487/04; C07D 513/04; C07D 498/04; A61K 31/41
[52] U.S. Cl. ..................................... 514/359; 514/366; 514/375; 548/151; 548/218; 548/257; 548/259; 548/261
[58] Field of Search ............... 548/151, 218, 257, 259, 548/261; 514/366, 375, 359

[56] References Cited

PUBLICATIONS

Terent'ev, Khim Geterotsikl Soedin, 1970, 770.

*Primary Examiner*—Robert Gerstl
*Attorney, Agent, or Firm*—Armstrong, Nikaido, Marmelstein, Kubovcik & Murray

[57] ABSTRACT

The present invention provides new tricyclic benzotriazoles of the general formula:

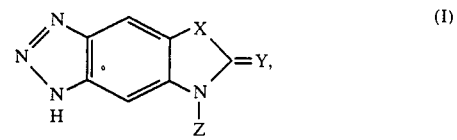

wherein Z is a hydrogen atom or an acyl radical, Y is an oxygen or sulphur atom or two hydrogen atoms and X is an oxygen or sulphur atom or a $>CR_1R_2$ or $>NR_3$ group, $R_1$ is a hydrogen atom or an alkyl, alkenyl or cycloalkyl radical, $R_2$ is a hydrogen atom or an alkyl, alkenyl or cyano group or a carbonyl group substituted by a hydroxyl, alkyl, alkoxy, amino, alkylamino, dialkylamino or hydrazino group or $R_2$, together with $R_1$, represents a cycloalkylene radical or $R_1$ and $R_2$ together form an alkylidene or cycloalkylidene radical and $R_3$ is a hydrogen atom or an alkyl radical; the tautomers thereof and the physiologically acceptable acid-addition salts thereof with inorganic and organic acids.

The present invention also provides processes for the preparation of these tricyclic benzotriazoles and pharmaceutical compositions containing them for the treatment of heart and circulatory diseases.

25 Claims, No Drawings

TRICYCLIC BENZOTRIAZOLES, PROCESSES FOR THE PREPARATION THEREOF AND PHARMACEUTICAL COMPOSITIONS CONTAINING THEM

The present invention is concerned with new tricyclic benzotriazoles, with processes for the preparation thereof and with pharmaceutical compositions containing them.

The new tricyclic benzotriazoles according to the present invention are compounds of the general formula:

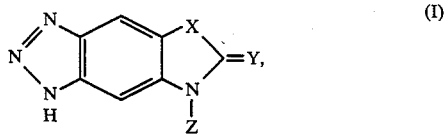

wherein Z is a hydrogen atom or an acyl radical, Y is an oxygen or sulphur atom or two hydrogen atoms, X is an oxygen or sulphur atom or a $>CR_1CR_2$ or $>NR_3$ group, $R_1$ is a hydrogen atom or an alkyl, alkenyl or cycloalkyl radical, $R_2$ is a hydrogen atom, an alkyl, alkenyl or cyano group or a carbonyl group substituted by a hydroxyl, alkyl, alkoxy, amino, alkylamino, dialkylamino or hydrazino group or together with $R_1$ represents a cycloalkylene group or $R_1$ and $R_2$ together form an alkylidene or cycloalkylidene radical and $R_3$ is a hydrogen atom or an alkyl radical; the tautomers thereof and the physiologically acceptable salts thereof with inorganic and organic acids.

Since the compounds of general formula (I) in which $R_1$ is not the same as $R_2$ contain an asymmetric carbon atom, the present invention also includes the optically-active forms and racemic mixtures of these compounds.

The new compounds according to the present invention possess valuable pharmacological properties and, in particular, they increase the strength of the heart and/or bring about a lowering of the blood pressure and/or influence the thrombocyte function and improve the microcirculation.

When, in general formula (I), X represents a $>CR_1R_2$ group, the substituents $R_1$ and $R_2$ can be the same or different, $R_1$ representing a hydrogen atom, an alkyl, cycloalkyl or alkenyl radical and $R_2$ representing a hydrogen atom, an alkyl, alkenyl or cyano group or a carbonyl group substituted by a hydroxyl, alkyl, amino, alkylamino, dialkylamino or hydrazino group, each of the mentioned alkyl and alkenyl moieties being straight-chained or branched and containing 1 to 6 or 2 to 6 carbon atoms, respectively, and the cycloalkyl moieties containing 3 to 7 carbon atoms.

Preferred in this meaning for $R_1$ and $R_2$, respectively, are hydrogen atoms and methyl, ethyl, isopropyl, 3-pentyl, allyl, cyclopentyl, cyclohexyl, cyano, acetyl, propionyl, methoxycarbonyl, ethoxycarbonyl, aminocarbonyl, methylaminocarbonyl, dimethylaminocarbonyl and hydrazinocarbonyl radicals.

$R_1$ and $R_2$, together with the carbon atom to which they are attached, can also form a cycloalkyl ring containing 3 to 7 carbon atoms, the spirocyclopropyl, spirocyclobutyl, spriocyclopentyl and spirocyclohexyl radicals thereby being preferred.

$R_1$ and $R_2$ together can also form an $C_1-C_6$ alkylidene or $C_3-C_7$ cycloalkylidene radical, the isopropylidene radical being preferred.

When, in general formula (I), X signifies an $>NR_3$ group, then $R_3$ is to be understood to be a hydrogen atom or a linear or branched alkyl chain containing up to 6 carbon atoms, the methyl, ethyl, propyl and butyl radicals being preferred.

When, in general formula (I), Z is an acyl radical, then this is to be understood to include linear aliphatic acyl radicals containing up to 3 carbon atoms, the acetyl radical being preferred.

Especially preferred compounds according to the present invention are those of general formula (I) in which Z is a hydrogen atom or an acetyl radical, Y is an oxygen or sulphur atom or two hydrogen atoms, X is an oxygen or sulphur atom or a $>CR_1R_2$ group, wherein $R_1$ and $R_2$ are the same and represent methyl or ethyl radicals or $R_1$ and $R_2$ are different and $R_1$ is a hydrogen atom or a methyl, ethyl, isopropyl or cyclopentyl radical and $R_2$ is a cyano, acetyl, methoxycarbonyl, ethoxycarbonyl, aminocarbonyl or hydrazinocarbonyl group or $R_1$ and $R_2$ represent a spriocyclopentyl ring when $R_1$ and $R_2$ form a cycloalkyl ring with the carbon atom to which they are attached or X represents an $NR_3$ group, in which $R_3$ is a hydrogen atom or a methyl or ethyl radical.

The compounds of general formula (I) according to the present invention can be prepared by processes known from the literature. However, the synthesis routes shown in the following schemes 1 to 3 are especially advantageous.

Scheme 1

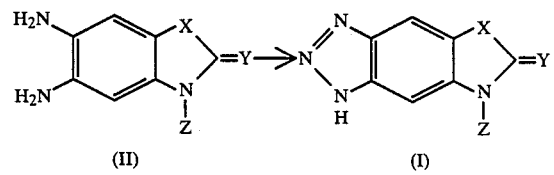

According to processes known from the literature (cf. F. R. Benson and W. L. Savell, Chemical Reviews, 46, 1/1950), the orthophenylenediamine derivatives of general formula (II), in which X, Y and Z have the above-given meanings, are reacted with nitrous acid, prepared from alkali metal nitrites, for example sodium nitrite, in acids, for example acetic acid, nitric acid or sulphuric acid, to give compounds of general formula (I), in which X, Y and Z have the above-given meanings. The reaction is carried out at a temperature of from $-20°$ C. to $+10°$ C., heating to $60°$ to $80°$ C., being carried out towards the end of the reaction for the completion thereof.

For the transfer of the third nitrogen atom to compounds of general formula (II), there can also be used diazonium salts, for example diazotised sulphanilic acid.

The compounds of general formula (II) are known from the literature or can be prepared by known processes (cf. published European patent application No. 0,161,632 and published Federal Republic of Germany patent application No. p 35 24 067.9).

Scheme 2

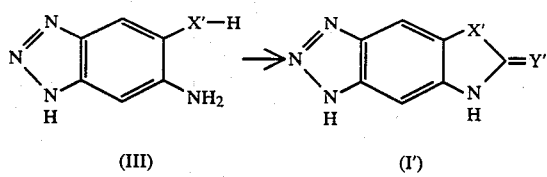

Compounds of general formula (I'), in which X' is an oxygen or sulphur atom or an >NR₃ group and Y' is an oxygen or sulphur atom, can be obtained from compounds of general formula (III), in which X' has the above-given meaning. For this purpose, they are reacted with reagents which transfer the carbonyl or thiocarbonyl group, for example phosgene, thiophosgene, N,N'-carbonyldiimidazole or urea (cf. E. S. Schipper and A. R. Day, in R. C. Elderfield (ed.), Heterocyclic Compounds, Vol. 5, pub. J. Wiley and Sons, New York, 1957, p. 284; J. W. Cornforth, ebenda, p. 439; and J. M. Sprague and A. H. Land, ebenda, p. 548).

The reaction with phosgene or thiophosgene is thereby preferably carried out in hydrochloric acid at ambient temperature and the reaction with N,N'-carbonyldiimidazole in boiling dioxan.

Scheme 3

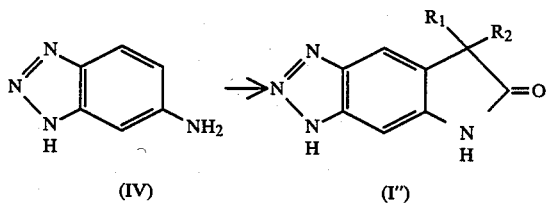

As an alternative to Scheme 1, the compounds of general formula (I'') can also be prepared by the oxindole synthesis route illustrated in Scheme 3 (cf. P. L. Julian, E. W. Mayer and H. C. Printy, in R. C. Elderfield (ed.), Heterocyclic Compounds, Vol. 3, pub. John Wiley and Sons, New York, pp. 128–142), for example by the Hinsberg synthesis: reaction of aromatic amines with the bisulphite addition compounds of ketones;

Brunner synthesis: cyclisation of aromatic amines via the hyrazide to oxindoles; and Stollé synthesis: cyclisation of aromatic amines via an amide to oxindoles.

Compounds of general formula (I) can also be subsequently converted into other compounds of general formula (I). This applies, for example, to the following cases:

(a) For the conversion of compounds of general formula (I), in which X has the above-given meaning, Z is a hydrogen atom and Y is an oxygen atom, into compounds of general formula (I), in which Y is a sulphur atom.

The reaction is carried out according to processes known from the literature with a reagent which transfers a sulphur atom, for example phosphorus pentasulphide, wherein preferably 1 to 5 mole but more preferably 1 mole of phosphorus pentasulphide are used per mole of compound (I), the reaction being carried out in an appropriate solvent, for example tetrahydrofuran, dioxan, benzene, toluene or pyridine, the reaction being carried out at a temperature of from 25° to 125° C.

However, it is preferred to use pyridine with a period of reaction of from 1 to hours and preferably of about 5 hours, depending upon the reaction component.

(b) For the conversion of compounds of general formula (I), in which X and Y have the above-given meanings and Z is an acyl radical, into compounds of general formula (I), in which Z is a hydrogen atom.

These hydrolyses are preferably carried out with acid or base catalysis in an appropriate solvent, for example water or aqueous ethanol. As acid, there can be used, for example, hydrochloric acid, sulphuric acid or phosphoric acid and, as base, an aqueous solution of sodium hydroxide or triethylamine.

(c) For the conversion of compounds of general formula (I), in which Y and Z have the above-given meanings and X is a >CR₁R₂ group, R₁ having the above-given meaning and R₂ being a carboxyl group, into compounds of the general formula (I), in which R₂ is a carbonyl group substituted by an alkoxy, amino, alkylamino, dialkylamino or hydrazino group.

This is preferably carried out by reacting a reactive derivative of the carboxylic acid, for example an acid chloride, with alcohols, primary or secondary amines, in a solvent, for example methylene chloride, diethyl ether, toluene or dimethylformamide, optionally in the presence of a base, for example triethylamine or pyridine, at a temperature of from −10° C. to the boiling temperature of the solvent. The conversion of carboxylic acid esters into amides or hydrazides is also preferably carried out in a solvent, such as ethanol, in the presence of 2 to 6 mole of a primary or secondary amine or of hydrazine hydrate at a temperature of from 20° to 100° C.

(d) For the conversion of compounds of general formula (I), in which Y and Z have the above-given meanings and X is a >CR₁R₂ group, R₁ having the above-given meaning and R₂ being an aminocarbonyl group, into compounds of general formula (I), in which R₂ is a cyano group.

The reaction to give the cyano group is preferably carried out in an inert solvent, for example methylene chloride, chloroform, dioxan, pyridine, xylene, chlorobenzene, in the presence of a water-removing agent, for example thionyl chloride, phosphorus oxychloride, phosphorus pentoxide, phosphorus pentachloride, aluminium chloride, benzenesulphonic acid chloride, toluenesulphonic acid chloride, triphenyl phosphine, boron trifluoride or polyphosphoric acid ethyl ester, at a temperature of from 50° to 250° C. but preferably at the boiling temperature of the solvent used.

(e) For the conversion of compounds of general formula (I), in which Y and Z have the above-given meanings and X is a >CR₁R₂ group, R₁ having the above-given meaning and R₂ being a cyano or alkoxy group, into compounds of general formula (I), in which R₂ is a carboxyl group or a hydrogen atom.

These hydrolyses are preferably carried out either in the presence of an acid, such as hydrochloric acid, sulphuric acid, phosphoric acid or trichloroacetic acid, or in the presence of a base, such as sodium hydroxide or potassium hydroxide, in an appropriate solvent, for example water, water/methanol, ethanol, water/ethanol, water/isopropanol or water/dioxan, at a temperature of from −10° C. to +120° C., for example at a temperature between ambient temperature and the boiling temperature of the reaction mixture.

This saponification is followed by a spontaneous decarboxylation when working at an elevated temperature, for example at the boiling point of the solvent or solvent mixture.

(f) For the conversion of compounds of general formula (I), in which $R_1$ and $R_2$ are hydrogen atoms, into compounds of general formula (I), in which $R_1$, together with $R_2$, signifies an isopropylidene, cyclopentylidene or cyclohexylidene group, as well as optionally a hydrogenation thereof to give the corresponding compounds of general formula (I), in which $R_1$ or $R_2$ is a hydrogen atom.

This concerns, for example, the reaction with compounds of the general formula:

$$R_4-CO-R_5 \qquad (V),$$

wherein $R_4$ and $R_5$ are alkyl radicals or $R_4$ and $R_5$ together form a $C_3-C_7$-cycloalkylene group, in the presence of a base, for example ammonia or triethylamine, in alcoholic solution.

Furthermore, the compounds obtained of general formula (I) can, if desired, be subsequently converted into their physiologically acceptable acid-addition salts with inorganic and organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid and methanesulphonic acid.

As already mentioned initially, the new compounds of general formula (I), the tautomers thereof and the physiologically acceptable acid-addition salts thereof display, with a long period of action, superior pharmacological properties, especially a blood pressure-lowering and/or positive inotropic action and/or influence the thrombocyte function and improve the microcirculation.

The inotropic action of certain compounds of the invention was determined in vivo according to the procedure reported below.

Male Sprague-Dawley rats weighing between 350 and 450 g were narcotized by intraperitoneal injection of a barbiturate and fitted with instrumentation for the examinations as described below:

A pressure measuring catheter (Miller Mikrotip/-diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on an electronically heated and thermostatically controlled operating table.

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positive inotropic effect $(dp/dt)_{60}$ were calculated. In addition, as criterion for the effectiveness of the substances, the maximum effect obtained (maximal increase of $(dp/dt)_{60}$) and its corresponding dose were determined. The table that follows reports the equipotent doses ($ED_{1,5}$=the dose in mg/kg that leads to an increase of $(dp/dt)_{60}$ of 1.5 mHg/sec) and the maximal effectiveness ($W_{max}$=the maximal increase of $(dp/dt)_{60}$), and the dose producing the maximum effectiveness.

| Substance from Exp. | $ED_{1,5}$ mHg/sec [mg/kg i.v.] | $W_{max}$ [mHg/sec] | [mg/kg i.v.] |
|---|---|---|---|
| Example 1 | 0,18 | 2,56 | 1,0 |
| Example 3 | >3 | 1,42 | 3,0 |
| Example 4 | >3 | 0,22 | 0,1 |

The compounds of Examples 1, 3 and 4 produced a low rate of pressure increase. The compounds of the present invention had a gentle inotropic effect upon the heart. This can in many instances be advantageous, as the compounds of the present invention require less critical measurements of dosage levels during administration to a patient with a weak heart.

From the results obtained to date, it appears that the most active compounds are compounds wherein X is $>CR_1R_2$ or $>NR_3$, $R_1$ and $R_2$ are $C_1-C_3$ alkyl, $R_3$ is $C_1-C_6$ alkyl, Z is hydrogen, and Y is an oxygen atom.

For the preparation of pharmaceutical compositions, the compounds according to the present invention are mixed in the usual manner with appropriate pharmaceutical carrier substances, aroma, flavouring and colouring materials and formed, for example, into tablets or dragees or, with the addition of appropriate adjuvants, suspended or dissolved in water or in an oil, for example olive oil.

The new compounds according to the present invention of general formula (I) and the salts thereof can be administered enterally or parenterally in liquid or solid form. As injection medium, it is preferred to use water which contains the additives usual in the case of injection solutions, for example stabilising agents, solubilising agents or buffers.

Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 1 to 500 mg. per day, referred to a body weight of 75 kg. It is preferred to administer 2 to 3 times a day 1 or 2 tablets with a content of active material of from 1 to 200 mg. The tablets can also be retarded in which case only 1 or 2 tablets with 1 to 500 mg. of active material have to be given once per day. The active material can also be administered by injection 1 to 8 times per day or by continuous infusion, in which case amounts of from 1 to 500 mg. per day normally suffice.

Apart from the compounds described in the following Examples, preferred compounds according to the present invention include the following and the tautomers thereof:

6,7-dihydro-1H,5H-pyrrolo[2,3-f]benzotriazol-6-one
7-ethyl-6,7-dihydro-1H,5H-pyrrolo[2,3-f]benzotriazol-6-one
7-n-propyl-6,7-dihydro-1H,5H-pyrrolo[2,3-f]benzotriazol-6-one
7-isopropyl-6,7-dihydro-1H,5H-pyrrolo[2,3-f]benzotriazol-6-one
7,7-diethyl-6,7-dihydro-1H,5H-pyrrolo[2,3-f]benzotriazol-6-one
7-methyl-7-ethoxycarbonyl-6,7-dihydro-1H,5H-pyrrolo[2,3-f]benzotriazol-6-one
7-ethoxycarbonyl-6,7-dihydro-1H,5H-pyrrolo[2,3-f]benzotriazol-6-one
7-methyl-7-aminocarbonyl-6,7-dihydro-1H,5H-pyrrolo[2,3-f]benzotriazol-6-one
7-aminocarbonyl-6,7-dihydro-1H,5H-pyrrolo[2,3-f]benzotriazol-6-one
7-methyl-7-hydrazinocarbonyl-6,7-dihydro-1H,5H-pyrrolo[2,3-f]benzotriazol-6-one
7-hydrazinocarbonyl-6,7-dihydro-1H,5H-pyrrolo[2,3-f]benzotriazol-6-one
7-methyl-7-acetyl-6,7-dihydro-1H,5H-pyrrolo[2,3-f]benzotriazol-6-one
7-methyl-7-cyano-6,7-dihydro-1H,5H-pyrrolo[2,3-f]benzotriazol-6-one
7-cyano-6,7-dihydro-1H,5H-pyrrolo[2,3-f]benzotriazol-6-one
spiro[cyclohexane-1,7'-6',7'-dihydro-3'H,5'H-pyrrolo[2',3'-f]benzotriazol]-6'-one
spiro[cyclopropane-1,7'-6',7'-dihydro-3'H,5'H-pyrrolo[2',3'-f]triazol]-6'-one
7-ethyl-1,5,6,7-tetradhydroimidazo[4,5-f]benzotriazol-6-one
7-propyl-1,5,6,7-tetrahydroimidazo[4,5-f]benzotriazol-6-one
7,7-dimethyl-6,7-dihydro-1H,5H-pyrrolo[2,3-f]benzotriazol-6-thione
7-methyl-1,5,6,7-tetrahydroimidazo[4,5-f]benzotriazol-6-thione
5,6-dihydro-1H-oxazolo[4,5-f]benzotriazol-6-thione
5,6-dihydro-1H-thiazolo[4,5-f]benzotriazol-6-thione
7-ethoxycarbonyl-7-methyl-6,7-dihydro-1H,5H-pyrrolo[2,3-f]benzotriazol-6-one.

The following Examples are given for the purpose of illustrating the present invention:

EXAMPLE 1

7,7-Dimethyl-6,7-dihydro-1H,5H-pyrrolo[2,3-f]benzotriazol-6-one 240 mg. (3.5 mMole) sodium nitrite were added portionwise to a suspension of 570 mg. (3 mMole) 5,6-diamino-3,3-dimethylindolin-2-one in 6 ml. 1N hydrochloric acid, the temperature being maintained between 0° and 5° C. by ice cooling. A red solution is obtained which is heated to 50° to 60° C. for 5 minutes. After cooling to ambient temperature, the crystalline precipitate obtained is filtered off with suction and washed with water. There are obtained 380 mg. of the title compound in the form of red crystals; m.p. 288°–291° C. (decomp.).

EXAMPLE 2

7-Methyl-6,7-dihydro-1H,5H-pyrrolo[2,3-f]benzotriazol-6-one

This compound, which has a melting point of >300° C., is obtained in a yield of 12% of theory in a manner analogous to that described in Example 1 from 5,6-diamino-3-methylindolin-2-one after column chromatographic purification (silica gel; dichloromethane/methanol 95:5 v/v) and recrystallisation from isopropanol.

EXAMPLE 3

Spriro[cyclopentan-1,7'-6',7'-dihydro-1'H,5'H-pyrrolo[2,3-f]benzotriazol]-6'-one This compound, which has a melting point of 271°–272° C. (decomp.), is obtained in a yield of 34% of theory in a manner analogous to that described in Example 1 from 5',6'-diamino-spiro[cyclopentane-1,3'-indolin]-2'-one after column chromatographic purification and recrystallisation from ethyl acetate.

EXAMPLE 4

5,6-Dihydro-1H-oxazolo[4,5-f]benzotriazol-6-one

This compound is obtained in a yield of 16% of theory from 5,6-diaminobenzoxazolin-2-one in a manner analogous to that described in Example 1. After column chromatographic purification (silica gel 60, dichloromethane/methanol/glacial acetic acid 10:1:0.2 v/v/v) and stirring with ethyl acetate, the compound has a melting point of >360° C.

EXAMPLE 5

7-Methyl-1,5,6,7-tetrahydroimidazo[4,5-f]benzotriazol-6-one

This compound, which has a melting point of >300° C., is obtained in a yield of 23% of theory in a manner analogous to that described in Example 1 from 5,6-diamino-1-methylbenzimidazolin-2-one after column chromatographic purification (silica gel; dichloromethane/methylene chloride 95:5 v/v) and recrystallisation from methanol.

EXAMPLE 6

5,6-Dihydro-1H-thiazolo[4,5-f]benzotriazol-6-one

This compound, which has a melting point of 355°–360° C. (decomp.), is obtained in a yield of 13% of theory in a manner analogous to that described in Example 1 from 5,6-diaminobenzothiazolin-2-one after column chromatographic purification (silica gel; butanol/acetic acid/water 4:1:5 v/v/v, lower phase discarded).

EXAMPLE 7

5-Acetyl-7,7-dimethyl-6,7-dihydro-1H,5H-pyrrolo[2,3-f]benzotriazole

A solution of 2.0 g. (9.1 mMole) 1-acetyl-5,6-diamino-3,3-dimethylindoline dihydrochloride, 6 ml. water and 1.8 ml. acetic acid is cooled to 0° C. and mixed with a solution of 0.62 g. (9.1 mMole) sodium nitretein 1 ml. water. The reaction mixture is stirred for 1 hour at ambient temperature, diluted with 5 ml. water and filtered. There are obtained 1.4 g. (67% of theory) of the title compound; m.p. 281°–283° C.

EXAMPLE 8

7,7-Dimethyl-6,7-dihydro-1H,5H-pyrrolo[2,3-f]benzotriazole dihydrochloride 0.5 g. of the product of Example 7 is heated under reflux for 2.5 hours with 20 ml. ethanolic hydrogen chloride solution, then allowed to cool and filtered. There is obtained 0.4 g. (70% of theory) of the title compound; m.p. 243°–245° C.

We claim:

1. Tricyclic benotriazole of the formula:

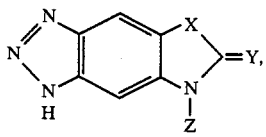
(I)

wherein
- Z is a hydrogen atom or a $C_1$–$C_3$ linear aliphatic acyl radical,
- Y is an oxygen or sulphur atom or two hydrogen atoms,
- and X is an oxygen or sulphur atom or $>NR_3$ group wherein
- $R_3$ is a hydrogen atom or a $C_1$–$C_6$ alkyl radical; and the tautomers thereof and the physiologically acceptable salts thereof with inorganic and organic acids.

2. Tricyclic benzotriazole of the formula:

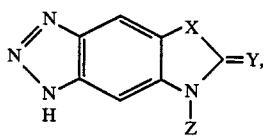
(I)

wherein
- Z is a hydrogen atom or a $C_1$–$C_3$ linear aliphatic acyl radical,
- Y is an oxygen or sulphur atom or two hydrogen atoms,
- and X is a $>CR_1R_2$ group, wherein
- $R_1$ is a hydrogen atom or a $C_1$–$C_6$ alkyl, $C_2$–$C_6$ alkenyl or $C_3$–$C_7$ cycloalkyl radical,
- $R_2$ is a $C_1$–$C_6$ alkyl, $C_2$–$C_6$ alkenyl or cyano group or a carbonyl group substituted by a hydroxyl, $C_1$–$C_6$ alkyl, $C_1$–$C_6$ alkoxy, amino, ($C_1$–$C_6$ alkyl) amino, di($C_1$–$C_6$ alkyl) amino or hydrazino group or
- $R_1$ and $R_2$, together with the carbon atom to which they are attached, represent a $C_3$–$C_7$ cycloalkylene group or
- $R_1$ and $R_2$ together form a $C_1$–$C_6$ alkyl radical; and the tautomers thereof and the physiologically acceptable salts thereof with inorganic and organic acids.

3. Tricyclic benzotriazole of the formula:

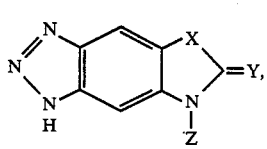
(I)

wherein
- Z is a hydrogen atom or a $C_1$–$C_3$ linear aliphatic acyl radical,
- Y is an oxygen or sulphur atom,
- and X is a $CR_1R_2$ group, wherein
- $R_1$ is a hydrogen atom, or a $C_1$–$C_6$ alkyl, $C_2$–$C_6$ alkenyl or $C_3$–$C_7$ cycloalkyl radical,
- $R_2$ is a hydrogen atom; and the tautomers thereof and the physiologically acceptable salts thereof with inorganic and organic acids.

4. Tricyclic benzotriazole of the formula:

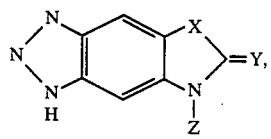
(I)

wherein
- Z is a hydrogen atom,
- Y is an oxygen or sulphur atom or two hydrogen atoms,
- and X is an oxygen or sulphur atom or a $CR_1R_2$ or $NR_3$ group, wherein
- $R_1$ is a hydrogen atom or a $C_1$–$C_6$ alkyl, $C_2$–$C_6$ alkenyl or $C_3$–$C_7$ cycloalkyl radical,
- $R_2$ is a hydrogen atom or a $C_1$–$C_6$ alkyl, $C_2$–$C_6$ alkenyl or cyano group or a carbonyl group substituted by a hydroxyl, $C_1$–$C_6$ alkyl, $C_1$–$C_6$ alkocy, amino, ($C_1$–$C_6$ alkyl)amino, di($C_1$–$C_6$-alkyl)amino or hydrazino group, or
- $R_1$ and $R_2$, together with the carbon atom to which they are attached, represent a $C_3$–$C_7$ cycloalkylene group or
- $R_1$ and $R_2$ together form a $C_1$–$C_6$ alkylidene or $C_3$–$C_7$ cycloalkylidene group, and
- $R_3$ is a hydrogen atom or a $C_1$–$C_6$ alkyl radical; and the tautomers thereof and the physiologically acceptable acceptable salts thereof with inorganic and organic acids.

5. Tricyclic benzotriazole of claim 1, 2, or 4, wherein
- Z is a hydrogen atom or an acetyl radical,
- Y is an oxygen or sulphur atom or two hydrogen atoms, and
- X is an oxygen or sulphur atom or a $>CR'_1R'_2$ group, wherein
- $R'_1$ and $R'_2$ are either the same and represent methyl or ethyl radicals, or $R'_1$ and $R'_2$ are different, with $R'_1$ being a hydrogen atom or a methyl, ethyl, isopropyl or cyclopentyl radical, and $R'_2$ being cyano, acetyl, methoxycarbonyl, ethoxycarbonyl, aminocarbonyl or hydrazinocarbonyl, or $R'_1$ and $R'_2$, together with the carbon atom to which they are attached, represent a spriocyclopentyl ring,
- or X is an $>NR'_3$ group wherein
- $R'_3$ is a hydrogen atom or a methyl or ethyl radical; and
- the tautomers thereof and the physiologically-acceptable salts thereof with inorganic and organic acids.

6. Tricyclic benzotriazole of claim 1, 3, or 4, wherein
- Z is a hydrogen atom or an acetyl radical,
- Y is an oxygen atom or two hydrogen atoms and
- X is an oxygen or sulphur atom or a $>CR''_1R''_2$ or $>NR''_3$ group, wherein
- $R''_1$ and $R''_2$ are hydrogen atoms or methyl radicals or $R''_1$ and $R''_2$, together with the carbon atom to which they are attached, form a spirocyclopentyl ring, and R''₃ is a hydrogen atom or a methyl radical; and the tautomers thereof and the physiologically-acceptable salts thereof with inorganic and organic acids.

7. Tricyclic benzotriazole of claim 2, 3, or 4, wherein R₁ and R₂ are independently selected from the group consisting of hydrogen, methyl, ethyl, isopropyl, 3-pentyl, allyl, cyclopentyl, cyclohexyl, cyano, acetyl, propionyl, methoxycarbonyl, ethoxycarbonyl, aminocarbonyl, methylaminocarbonyl, dimethylaminocarbonyl and hydrazinocarbonyl, or together are isopropylidene.

8. Tricyclic benzotriazole of claim 2, 3, or 4, wherein R₁ and R₂, together with the carbon atom to which they are attached, are selected from the group consisting of spirocyclopropyl, spirocyclobutyl, spirocyclopentyl, and spirocyclohexyl.

9. Tricyclic benzotriazole of claim 1 or 4, wherein X is >NR'''₃ and R''' is selected from the group consisting of methyl, ethyl, propyl and butyl.

10. Tricyclic benzotriazole of claim 1, 2, or 3, wherein Z is acetyl.

11. Tricyclic benzotriazole of claim 2, wherein the tricyclic benzotriazole is 7,7-dimethyl-6,7-dihydro-1H,5H-pyrrolo[2,3-f]benzotriazol-6-one.

12. Tricyclic benzotriazole of claim 2, wherein the tricyclic benzotriazole is spiro[cyclopentan-1,7'-6',7'-dihydro-1'H,5'H-pyrrolo[2',3'-f]benzotriazol]-6'-one.

13. Tricyclic benzotriazole of claim 1, wherein the tricyclic benzotriazole is 5,6-dihydro-1H-oxazolo[4,5-f]benzotriazol-6-one.

14. Tricyclic benzotriazole selected from the group consisting of:
6,7-dihydro-1H,5H-pyrrolo[2,3-f]benzotriazol-6-one
7-ethyl-6,7-dihydro-1H,5H-pyrrolo[2,3-f]benzotriazol-6-one
7-n-propyl-6,7-dihydro-1H,5H-pyrrolo[2,3-f]benzotriazol-6-one
7-isopropyl-6,7-dihydro-1H,5H-pyrrolo[2,3-f]benzotriazol-6-one
7,7-diethyl-6,7-dihydro-1H,5H-pyrrolo[2,3-f]benzotriazol-6-one
7-methyl-7-ethoxycarbonyl-6,7-dihydro-1H,5H-pyrrolo[2,3-f]benzotriazol-6-one
7-ethoxycarbonyl-6,7-dihydro-1H,5H-pyrrolo[2,3-f]benzotriazol-6-one
7-methyl-7-aminocarbonyl-6,7-dihydro-1H,5H-pyrrolo[2,3-f]benzotriazol-6-one
7-aminocarbonyl-6,7-dihydro-1H,5H-pyrrolo[2,3-f]benzotriazol-6-one
7-methyl-7-hydrazinocarbonyl-6,7-dihydro-1H,5H-pyrrolo[2,3-f]benzotriazol-6-one
7-hydrazinocarbonyl-6,7-dihydro-1H,5H-pyrrolo[2,3-f]benzotriazol-6-one
7-methyl-7-acetyl-6,7-dihydro-1H,5H-pyrrolo[2,3-f]benzotriazol-6-one
7-methyl-7-cyano-6,7-dihydro-1H,5H-pyrrolo[2,3-f]benzotriazol-6-one
7-cyano-6,7-dihydro-1H,5H-pyrrolo[2,3-f]benzotriazol-6-one spiro[cyclohexane-1,7'-6',7'-dihydro-3'H,5'H-pyrrolo[2',3'-f]benzotriazol]-6'-one
spiro[cyclopropane-1,7'-6',7'-dihydro-3'H,5'H-pyrrolo[2',3'-f]triazol]-6'-one
7-ethyl-1,5,6,7-tetrahydroimidazo[4,5-f]benzotriazol-6-one
7-propyl-1,5,6,7-tetrahydroimidazo[4,5-f]benzotriazol-6-one
7,7-dimethyl-6,7-dihydro-1H,5H-pyrrolo[2,3-f]benzotriazol-6-thione
7-methyl-1,5,6,7-tetrahydroimidazo[4,5-f]benzotriazol-6-thione
5,6-dihydro-1H-oxazolo[4,5-f]benzotriazol-6-thione
5,6-dihydro-1H-thiazolo[4,5-f]benzotriazol-6-thione
7-ethoxycarbonyl-7-methyl-6,7-dihydro-1H,5H-pyrrolo-[2,3-f]benzotriazol-6-one.

15. Tricyclic benzotriazole of claim 4, wherein Z is hydrogen, Y is oxygen, and X is >CR₁R₂ or >NR₃, wherein R₁ and R₁ are independently C₁-C₃ alkyl and R₃ is C₁-C₆ alkyl.

16. Pharmaceutical composition for reducing blood pressure, producing a positive inotropic action, influencing thrombocyte aggregation, or improving microcirculation, comprising a pharmaceutically acceptable carrier or diluent and an effective amount of a tricyclic benzotriazole of the formula:

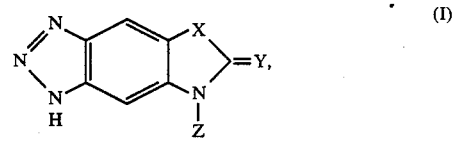

wherein
Z is a hydrogen atom or a C₁-C₃ linear aliphatic acyl radical,
Y is an oxygen or sulphur atom or two hydrogen atoms,
and X is an oxygen or sulphur atom or CR₁R₂ or NR₃ group wherein
R₁ is a hydrogen atom or a C₁-C₆ alkyl, C₂-C₆ alkenyl or C₃-C₇ cycloalkyl radical,
R₂ is a hydrogen atom or a C₁-C₆ alkyl, C₂-C₆ alkenyl or cyano group or a carbonyl group substituted by a hydroxyl, C₁-C₆ alkyl, C₁-C₆ alkoxy, amino, (C₁-C₆ alkyl) amino, di(C₁-C₆ alkyl)amino or hydrazino group or
R₁ and R₂, together with the carbon atom to which they are attached, represent a C₃-C₇ cycloalkylene group or
R₁ and R₂ together form a C₁-C₆ alkylidene or C₃-C₇ cycloalkylidene group, and
R₃ is a hydrogen atom or a C₁-C₆ alkyl radical; and the tautomers thereof and the physiologically acceptable salts thereof with inorganic and organic acids.

17. Method of reducing blood pressure in a patient in need of such reduction, said method comprising administering to said patient an effective amount of a compound of claim 1, 2, or 4.

18. Method of producing a positive inotropic action in a patient in need of such action, said method comprising administering to said patient an effective amount of a compound of claim 1, 2, 3, or 4.

19. A method of influencing thrombocyte aggregation in a patient in need of such influence, said method comprising administering to said patient an effective amount of a compound of claim 1, 2, 3, or 4.

20. A method of improvising microcirculation in a patient in need of such improvement, said method comprising administering to said patient an effective amount of a compound of claim 1, 2, 3, or 4.

21. Method of claim 17, wherein said amount is about 1 to 50 mg per day.

22. Method of claim 18, wherein said amount is about 1 to 50 mg per day.

23. Method of claim 19, wherein said amount is about 1 to 50 mg per day.

24. Method of claim 20, wherein said amount is about 1 to 50 mg per day.

25. Composition of claim 16, wherein said composition is in the form of a tablet containing 0.5 to 20 mg of said compound.

* * * * *